(12) United States Patent
Kirsner

(10) Patent No.: US 7,771,366 B2
(45) Date of Patent: Aug. 10, 2010

(54) VAGINAL FERTILITY PROBE

(76) Inventor: Vaclav Kirsner, 83 Davis Ranch Rd., Bellvue, CO (US) 80512

( * ) Notice: Subject to any disclaimer, the term of this patent is extended or adjusted under 35 U.S.C. 154(b) by 1023 days.

(21) Appl. No.: 10/610,115

(22) Filed: Jun. 30, 2003

(65) Prior Publication Data
US 2005/0256423 A1    Nov. 17, 2005

Related U.S. Application Data

(60) Provisional application No. 60/392,551, filed on Jul. 1, 2002.

(51) Int. Cl.
*A61B 10/00* (2006.01)
*A61B 5/05* (2006.01)
*A61B 5/103* (2006.01)
*A61B 5/117* (2006.01)

(52) U.S. Cl. .................. 600/551; 600/547; 600/591; 600/587

(58) Field of Classification Search ............... 600/551, 600/547, 591, 587
See application file for complete search history.

(56) References Cited

U.S. PATENT DOCUMENTS

| | | | | |
|---|---|---|---|---|
| 3,297,020 A | * | 1/1967 | Mathiesen | 600/551 |
| 3,749,089 A | * | 7/1973 | Derr | 600/345 |
| 3,844,276 A | * | 10/1974 | McDougall | 600/373 |
| 4,224,949 A | * | 9/1980 | Scott et al. | 600/373 |
| 4,498,481 A | * | 2/1985 | Lemke | 600/547 |
| 4,685,471 A | * | 8/1987 | Regas et al. | 600/547 |
| 4,753,247 A | * | 6/1988 | Kirsner | 600/547 |
| 4,770,186 A | * | 9/1988 | Regas et al. | 600/547 |
| 5,240,010 A | * | 8/1993 | Weinmann | 600/547 |
| 5,916,173 A | * | 6/1999 | Kirsner | 600/551 |
| 6,174,290 B1 | * | 1/2001 | Cho | 600/551 |

* cited by examiner

*Primary Examiner*—Max Hindenburg
*Assistant Examiner*—Jeffrey G Hoekstra
(74) *Attorney, Agent, or Firm*—Craig R. Miles; CR Miles, P.C.

(57) ABSTRACT

A method for tissue bioassay comprising the steps of placing in the vagina of a female mammal an elongated probe having at least two electrodes positioned close to an insertion end of the probe, none of the electrodes extending around the entire periphery of said probe and at least one of then being metallic, applying across the electrodes an alternating voltage of relatively low peak-to-peak amplitude, measuring across the electrodes a value representative of the phase of the reproductive cycle of the female or the hormonal status of the fornix epithelium, and comparing that value with at least one reference value. A probe for practicing this method also is disclosed.

5 Claims, 8 Drawing Sheets

VAGINAL FERTILITY PROBE

This U.S. patent application Ser. No. 10/610,115, filed Jun, 30, 2003, claims the benefit of U.S. patent application No. 60/392,551, filed Jul. 1, 2002.

BACKGROUND OF THE INVENTION

1. Field of the Invention

The present invention relates to vaginal fertility probes and in particular to new probes and associated methods of use. The probes of the present invention provide an electronic device that monitors the endocrinological/physiological status of epithelial tissues in the posterior fornix of the vagina.

More particularly, this invention relates to a probe for predicting and detecting ovulation in mammals, particularly in human females, and to a method of predicting and detecting ovulation that is based solely on the vaginal steady-state measurements of an epithelium-responsive parameter such as alternating current or admittance.

The invention also pertains to a bioassay for pharmacokinetic measurements of hormone replacement therapy in menopausal women, and to the monitoring of other therapies employed in women's health care. The invention also relates to a method and apparatus for women's self-administered health-awareness monitoring.

2. Discussion of the Related Art

U.S. Pat. No. 4,753,247 (Kirsner, Jun. 28, 1988) discloses that measurements of the surface admittance or of the alternating current, performed with non-metallic, and particularly vitreous (or glassy) carbon, electrodes in the posterior fornix of the human vagina, provide a good prediction as well as detection of ovulation. The capability to predict and then detect ovulation was afforded by the therein-presented repeatable cyclic profiles of the probe readings, which exhibited a number of peaks and dips reflecting significant cyclical variations in the recorded parameter.

The cyclic profiles were yielded by the daily probe measurements of the current output from the electrodes that were stimulated by a relatively high-frequency and decidedly low-amplitude alternating voltage. The electrode stimulation was supplied by a small, battery-powered, hand-held apparatus with a digital display for the current output readings. The readings were plotted in a graph against the day of cycle. To the woman-user or to her physician, such a graphical representation of the data would be reminiscent of the graphing of the familiar, if rather unsatisfactory, basal body temperature measurements for fertility assessment.

My '247 patent did not make it clear that, by the time the patent issued, the probe's ovulation-marker minimum had been demonstrated to coincide with the urinary luteinizing hormone (LH) marker of ovulation. W. F. Ganong, "Review of Medical Physiology", 17$^{th}$ edition, 1995 states that ovulation occurs about 9 hours after the LH surge in blood. The patent only showed that, as expected, the minimum invariably occurred before the rise in the woman's basal body temperature, which is indicative of ovulation having taken place before the temperature rise, consistent with the ovulation-marker minimum.

My 1988 '247 patent noted that the probe's ovulation marker minimum occurs at a time when the vaginal fluids are most conductive. Their increased conductivity is due to the well-known temporary abundance of mucous secretions with high water and salt content at around the time of ovulation. Significantly, the minimum in the probe admittance current is the inverse of that maximal conductivity. My patent made a point about this inverse relationship between the ovulation-marker drop in the probe current and the expected increase in the current that would have to be observed had metal electrodes been employed for conductivity or impedance measurement of the temporarily more conductive cervical mucus secretions.

I now reference examples of such metal electrode devices that yield otherwise featureless vaginal impedance cyclic profiles, exhibiting a simple mid-cycle minimum which is due to the temporarily increased conductivity (i.e., decreased resistance) of the vaginal fluids. This increase in conductivity of vaginal mucus had been published in the sixties and the seventies by farm animal reproduction scientists, and several U.S. patents utilizing that phenomenon were issued in the seventies and the eighties. McDougal, Scott et al. and Lemke (U.S. Pat. Nos. 3,844,276, 4,224,949 and 4,498,481, respectively).

The patents disclosed different electrode configurations, all designed to maximize the contact area with the vaginal fluids for the measurements that were performed with standard ohmmeters. Scott et al. discussed at length the theory of their measurement method and probe. Unlike McDougal and Lemke, they used relatively long rod-shaped electrodes (at least 1 inch and up to 4 inches in length, preferred 2 to 3½ inches). Their ohmmeter could provide AC current at frequency up to 1 MHz (preferred 5 to 100 kHz) and the peak-to-peak voltage between 1 Volt and 10 Volts and preferably between 3 and 6 Volts.

It was not considered in their disclosure that these are very high voltage levels that cause electrode reactions of electrolysis and release of toxic metal ions due to electrode dissolution, which is bound to be harmful to the reproductive tract, particularly at the lower frequencies. While they disclose wide ranges of voltage and frequency, the examples of their cow monitoring results were in fact generated with 3 volts peak-to-peak at 2.5 kHz. They used 3 inch long electrodes that were positioned approximately an inch away from the cervix and the fornix.

One example of the application of this conductometric approach to human fertility monitoring is the Cue Fertility Monitor from Zetek Corporation, which employs a multitude of ring-shaped metal electrodes and is covered by U.S. Pat. No. 4,685,471 (Regas et al., Aug. 31, 1987). Since their vaginal monitor's cyclic profile exhibited only one distinct feature, namely the mid-cycle decrease in vaginal resistance, which afforded no ovulation prediction, Zetek also provided for an additional separate measurement of the conductivity of saliva. Salivary resistance gave no indication of ovulation but it did give them a long-term predictive signal about a week before ovulation. While such a long-term predictive signal is of great potential significance, neither the oral nor more importantly the vaginal measurements with the Zetek Cue Fertility Monitor generated any short-term predictive signal such as is produced by the probe disclosed in my '247 patent. The Cue's vaginal resistance cyclic profile is also devoid of the other multiple features that were described in my prior art patent.

The other example is a very similar, even if somewhat simplified, vaginal probe device and technique akin to the Cue and disclosed in U.S. Pat. No. 5,240,010 (Weinmann, Aug. 31, 1993). The patent purports to solve the problem of absent predictive signals by the introduction of the fundamentally wrong and therefore discredited rhythm-method calculation into the software of the device. Weinmann's recourse to the rhythm method is illogical because had the rhythm method worked, there would be no need to obviate its use with new technological tools. In his patent, Weinmann refers to but does not describe his software as evaluating the same profile of vaginal impedance as the profile generated by the Zetek Cue Monitor; the undisclosed software would additionally utilize a temperature-rise signal to define the end of the fertile period.

Note that no similar recourse, to either an additional oral measurement or to a 15 rhythm method calculation or to a temperature measurement, has been necessary with my probe technology as disclosed in the '247 patent.

My '247 patent was based on the assumption that only the special vitreous (or glassy) carbon electrodes were able to perform the vaginal measurements in the claimed manner. The assumption was that only the glassy carbon electrodes (gce) would yield the unprecedented cyclic profiles with the distinct and multiple features that provide the most important capability to predict as well as to detect ovulation. At the time and until recently, I was convinced that, in addition to the importance of performing the measurements in the posterior fornix of the vagina, my probe measured greater variations during the menstrual cycle than any other vaginal monitoring technique because of my particular method of measurement (namely, admittance or alternating current response to a.c.-applied small potential difference of relatively high frequency), performed with the particular kind of electrode material that I used and patented.

I held that view for several reasons: a) because no other vaginal monitor yielded any multi-featured cyclic profile (and they all used electrode materials other than vitreous carbon): b) because the vitreous carbon was undoubtedly biocompatible and novel in the gynecological diagnostic application; c) because, in my opinion, the vitreous carbon electrode is electrochemically distinct from metal electrodes and from electrodes made of other forms of carbon such as graphite or carbon paste; and d) because I was a practitioner of modern bioelectrochemistry and its electrodic (as opposed to ionic) and fuel-cell concepts of physiological phenomena. In these concepts, the classical (equilibrium) Nernst equation and ionic mechanisms are replaced with the Butler-Volmer and/or Tafel (kinetic) formalization of electrodic measurements and mechanisms.

In brief, at the inception of the project I envisaged the epithelium of the posterior fornix to function in a manner similar to the membrane models later rationalized in academic literature (e.g., Electrochim. Acta, 34, 567, 1989; J. Biol. Phys. 14, 31, 1986; J. Bioelectrochem. 3, 247, 1984), basically as a network of microscopic biochemical fuel cells. My 247 patent gave an example of a conceivable redox reaction involved in the hypothetical electron transfer network, and stated that "while not wishing to be bound by theory, the present inventor believes that this is an example of many such reactions".

In the present application, I continue to maintain the position of not being bound by theory. However, I would add an important characteristic to my conceptual electrodic network, namely the susceptibility of some of the network components to at least some of the sex hormones and/or other chemicals involved in fertility cycling. A general example of such hormone-responsive electrodic components could be the enzymes that drive the cyclical changes in the composition of the epithelial cells and in the mucus secretions of the epithelia. Such enzymes could respond to the hormones by means of associated hormone-receptor sites. The genital tract is, in fact, known to be rich in the concentrations of the sex hormone receptors. Note that the classical concepts of ionics do not lend themselves to such responsiveness to hormones and other modulators. For more insight, the 1993 book "Surface Electrochemistry. A Molecular Level Approach" provides an eloquent account of the concepts and principles, including those of bioelectrochemistry, that inspired the design of the original Kirsner vaginal probe as a tool for scientific family planning.

SUMMARY OF THE INVENTION

In accordance with the inventions of the present application, a probe is provided which measures the alternating current or admittance in the posterior fornix of the mammalian vagina, using two steel electrodes that are stimulated with very low amplitude alternating voltage of high frequency. The probe is of such a length, diameter and shape as to place the electrodes in contact with a well-defined predetermined aspect of the epithelial tissues in the posterior fornix of the vagina. The probe disclosed in this application is an improvement on the probe described in my '247 patent.

The inventions of this application meet a number of objects:

One object of the inventions of this application is to improve the sensitivity and signal-to-noise characteristics of prior methods and apparatus for predicting and detecting ovulation in mammals in general and in women in particular.

Another object of the inventions is to increase the reliability and repeatability of fertility monitoring in the vagina.

Another object of the inventions is to monitor a parameter characteristic of the physiological and/or endocrinological status of the vaginal tissues.

Another object of the inventions is to enable the safe use of metallic electrodes, achieved by using electrode stimulation that avoids electrolytic damage of, or irritation to, the tissues in contact with the electrodes.

Another object of the inventions is to provide self-monitoring means for women pursuing health awareness.

Another object of the inventions is to provide a diagnostic tool for physicians, for example for the management of hormone replacement therapy or of the premenstrual syndrome.

A final object of the inventions is to improve the economic value of my own prior art apparatus by the use of a metal material and particularly an inexpensive and easily usable metal electrode material, although the use of noble metals is also within the scope of the inventions.

Inventions of this application comprise an improved method for monitoring fertility in women and a method of monitoring the hormonal status of the posterior fornix epithelia (collectively referred to as "tissue bioassay"). In either case, the method involves the following steps:

placing in the vagina a probe having two electrodes, orienting the probe so that contact is made with a well-defined predetermined region of the epithelium in the posterior fornix, measuring across the electrodes at least one physical parameter indicative of the phase of the menstrual cycle or of the tissue's hormonal status, respectively and/or synonymously (that is, doing both), and comparing the value with a reference value or values.

Preferred embodiments of this method include the following:

comparing the value with a reference value or values.

the measurement of alternating current, admittance or any of their components or derived or computed parameters across the electrodes, using for the electrode stimulation any of a number of conceivable waveforms such as but not limited to a sine-wave.

In another form, the method of my inventions involves the following steps:

placing in the vagina of a female mammal an elongated probe having at least two electrodes positioned close to an insertion end of said probe, none of the electrodes extending around the entire periphery of said probe and at least one of then being metallic, applying across the electrodes an alternating voltage of relatively low peak-to-peak amplitude, measuring across the electrodes a value representative of the phase of the reproductive cycle of the female or the hormonal status of the fornix epithelium, and comparing that value with at least one reference value.

Preferred versions of this method include:

use of a voltage having a peak-to-peak amplitude in the range of from about 10 millivolts to about 900 millivolts.

positioning the probe so that at least one of its electrodes contacts the cervix or the fornix epithelium.

selecting a physical parameter from the group consisting of admittance, current and phase difference.

positioning at least one of the electrodes of the probe at the insertion end of the probe.

setting the distance between the insertion end of the probe and the proximal end of at least one of its electrodes so that it does not exceed about 100% to about 150% of the length of the cervical protrusion into the fornix region.

In another form, the method of these inventions involves the following steps:

placing in a biological system a probe having at least two electrodes positioned close to an insertion end of the probe, at least one of the electrodes being metallic, applying across the electrodes an alternating voltage of relatively low peak-to-peak amplitude, measuring across the electrodes the value of a physiological indicator of interest, and comparing said value with at least one reference value.

Preferred versions of this method include:

use of a voltage having a peak-to-peak amplitude in the range of from about 10 millivolts to about 900 millivolts.

positioning the probe so that at least one of its electrodes contacts the cervix or the fornix epithelium.

selecting a physical parameter from the group consisting of admittance, current and phase difference.

positioning at least one of the electrodes of the probe at the insertion end of the probe.

setting the distance between the insertion end of the probe and the proximal end of at least one of its electrodes so that it does not exceed about 100% to about 150% of the length of the cervical protrusion into the fornix region.

repeating the process at least daily for a period of at least two days, each time inserting the probe into the vagina in the same manner it was inserted on previous occasions to insure that its electrodes are positioned consistently with respect to the cervix and fornix epithelium.

The inventions of this applications further include a probe for performing a tissue bioassay comprising:

an elongated body of nonconducting material, at least two electrodes affixed close to an insertion end of the body, none of which extends around the entire periphery of the probe and at least one of which is metallic, means for imposing an alternating voltage or current of relatively small peak-to-peak amplitude across the electrodes, and means for measuring the voltage, current or phase difference across the electrodes.

Preferred embodiments of this probe include:

use of an input voltage in the range of from about 10 millivolts to about 900 millivolts peak-to-peak.

positioning of at least one electrode at the insertion end of the probe.

positioning of at least one electrodes so that the distance between the insertion end of the probe and the proximal end of the electrode does not exceed about 100% to 150% of the length of the cervical protrusion into the fornix region.

providing the elongated body with two flats at its electrode bearing end, each of which bears a flat, with each flat bearing an electrode.

The inventions of this applications also include a probe for performing a tissue bioassay comprising:

an elongated body of nonconducting material, at least two electrodes, and preferable two, affixed close to an insertion end of the body, at least one of which is metallic, means for imposing an alternating voltage or current across the electrodes, means for measuring across the electrodes a value representative of the phase of the reproductive cycle of the female or the hormonal status of the fornix epithelium, wherein the probe, when placed in the vagina of a female close to the fornix epithelium, displays a minimum of admittance when vaginal mucus displays a maximum of conductivity.

The inventions of this application further include a probe for performing a tissue bioassay comprising:

an elongated body of nonconducting material, at least two electrodes affixed close to an insertion end of the body, none of which extends around the entire periphery of the probe and at least one of which is metallic, means for imposing an alternating voltage or current of relatively small peak-to-peak amplitude across the electrodes, and means for measuring the voltage, current or phase difference across the electrodes.

Preferred embodiments of this probe include:

use of an input voltage in the range of from about 10 millivolts to about 900 millivolts peak-to-peak.

positioning of at least one electrode at the insertion end of the probe.

positioning of at least one electrodes so that the distance between the insertion end of the probe and the proximal end of the electrode does not exceed about 100% to 150% of the length of the cervical protrusion into the fornix region.

providing the elongated body with two flats at its electrode bearing end, each of which bears a flat, with each flat bearing an electrode.

The inventions of this applications also include a probe for performing a tissue bioassay comprising:

an elongated body of nonconducting material, at least two electrodes, and preferable two, affixed close to an insertion end of the body, at least one of which is metallic, means for imposing an alternating voltage or current across the electrodes, means for measuring across the electrodes a value representative of the phase of the reproductive cycle of the female or the hormonal status of the fornix epithelium, wherein the probe, when placed in the vagina of a female close to the fornix epithelium, displays a minimum of admittance when vaginal mucus displays a maximum of conductivity.

Although my inventions are readily adaptable for use with other female mammals, the methods and apparatus according to the inventions are of particular applicability to the prediction and detection of ovulation in the human female, as was the case with my '247 patent. In addition, the methods and apparatus of the inventions are applicable to tissues other than vaginal tissues. For example, they can be applied to other tissues of the body, including secretory tissues such as oral tissues. Other examples include rectal tissues and certain specific regions of the skin.

BRIEF DESCRIPTION OF THE DRAWINGS

The invention will be further described with reference to the accompanying drawings, in which.

DESCRIPTION OF THE PREFERRED EMBODIMENTS

Figure 1:
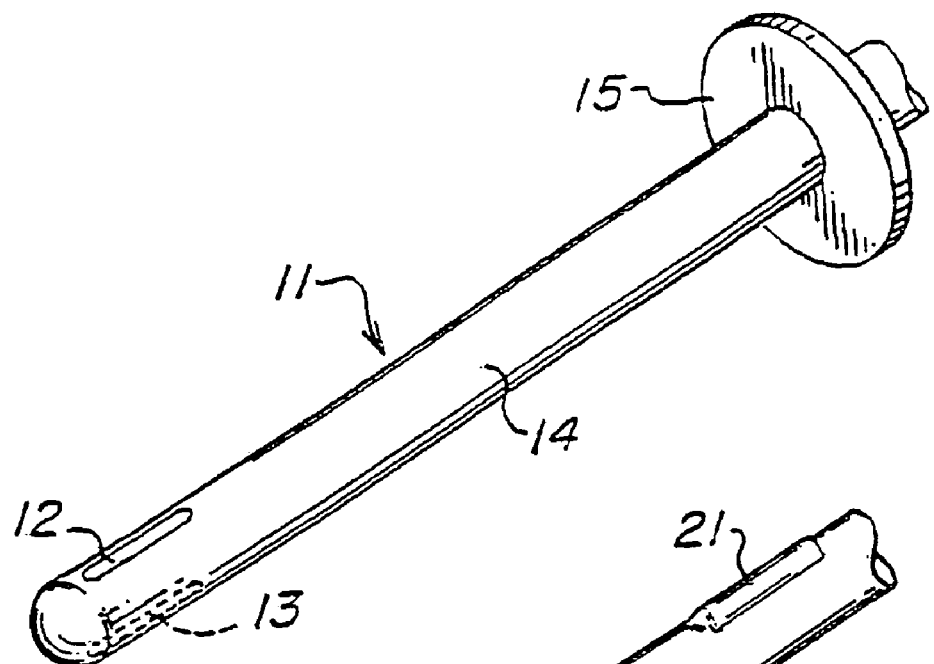
FIG. 1 depicts a vaginal probe of the prior art.

Referring now to the drawings in detail, FIG. 1 shows a vaginal probe of the prior art. In particular, it shows the probe of FIG. 2 of my U.S. Pat. No. 4,753,247. The probe 11 comprises a rigid or semi-rigid cylindrical body 14 (approximately 10 to 15 cms in length and 1 cm in diameter for human use) having rounded distal or insertion end insertable into the vagina, with the insertion end extending into the region of the posterior fornix. Two nonmetallic electrodes or elements 12 and 13 are attached to probe body 14. The electrodes 12 and 13 can be of any shape and size within reason. The attachment of electrodes 12 and 13 to body 14 can be accomplished by any method known for attaching an electrode to a substrate, including but not limited to gluing, bonding and embedding.

In the probe of the prior art depicted in FIG. 1, the proximal end element 15 of probe 11 is circular and featureless. There is no guide to orient the probe 11 during and after the process of insertion into the vagina. The electrode positioning within the posterior fornix is indeterminate.

Figure 2:
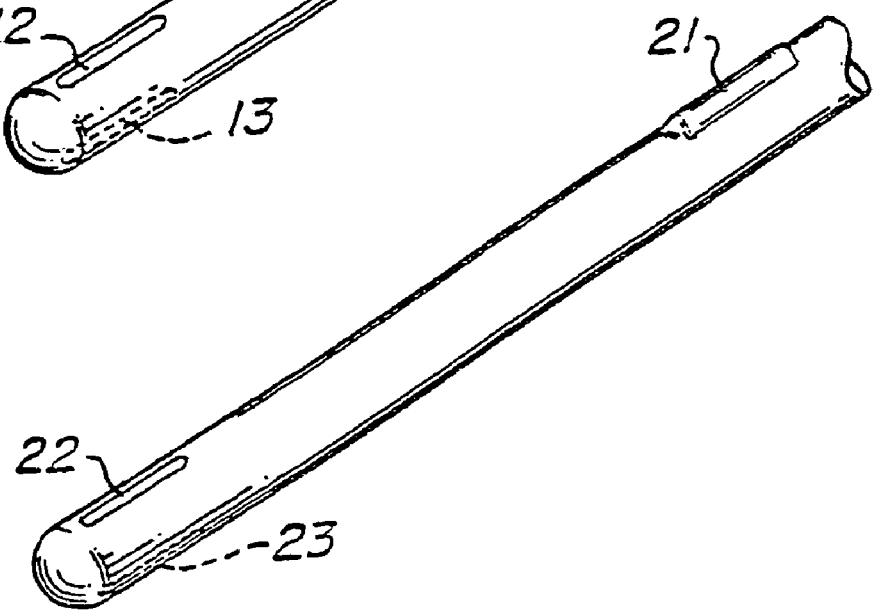
FIG. 2 depicts a vaginal probe of the invention having indicator means for positioning the probe in the vagina so that the marked electrode can be reproducibly placed in a defined position with respect to the cervix, in the posterior fornix of the vagina.

FIG. 2 depicts a probe of the invention which makes it possible to control the orientation of the sensor so that electrode contact is made with a defined predetermined aspect of the epithelia in the posterior fornix 31 (as shown in FIG. 3). The posterior fornix is conventionally defined as the small approximately half spherical or half cylindrical region at the very top of the human vagina above the cervix at the posterior or farther side of the cervix in a standing woman.

The probe has electrodes 22 and 23 disposed opposite one another at the insertion end of the probe. The electrodes need to be located on the probe so as to make contact in the fornix region. At a minimum, at least one electrode should be located close to the end of the probe, which means that the maximum distance from the end of the probe to the nearest edge of the electrode should be less than 10% to 25% of the protrusion length of the cervix as it protrudes into the vagina. Preferably, at least one electrode should be located at the end of the probe, which means that the .about. maximum distance from the end of the probe to the nearest edge of the electrode should be less than 10% of the protrusion length of the cervix as it protrudes into the vagina.

Indicator means in the form of an elongated protrusion 21 are lined up with electrode 22. Protrusion means 21 give the user a definite guide to orient the probe during and after the process of insertion into the vagina.

Figure 3A:
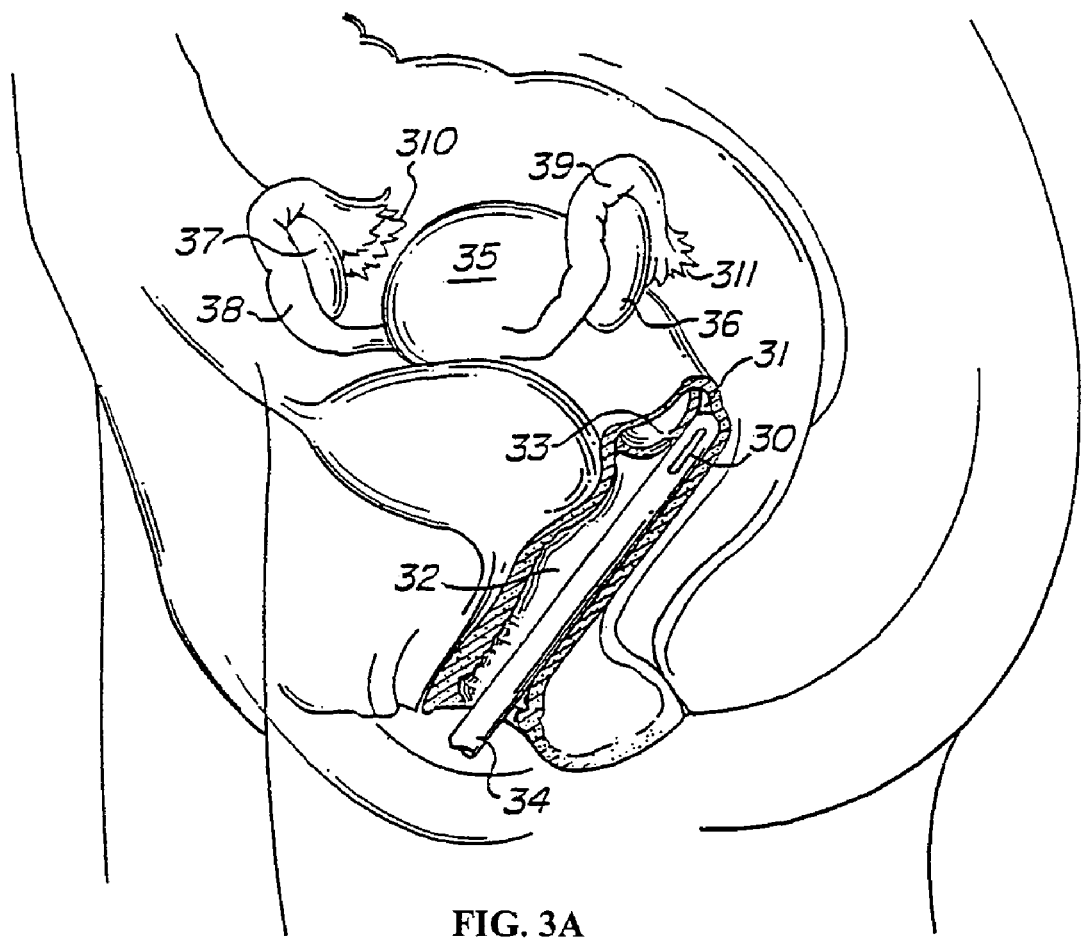
FIGS. 3A and 3B depict the vaginal probe of FIG. 2 inserted in the posterior fornix of the vagina of a human female in two different electrode-orientation positions.
Figure 3B:
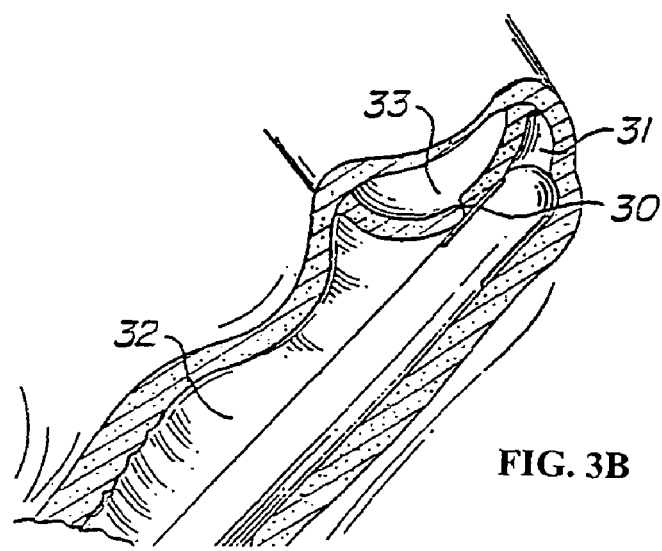

This can be understood with the help of FIGS. 3A and 3B, which show the anatomical arrangement of the genital tract of a human female in a side view. FIGS. 3A and 3B show the posterior fornix region 31 at the upper end of the vaginal canal 32 into which extends the approximately semispherical, conical or cylindrical protrusion of the cervix 33. Observe the manner in which the cervix protrudes into the vagina creating two vaginal folds in the anterior and posterior vaginal fornices. The posterior fornix is larger and more easily accessible than the anterior fornix.

FIG. 3A depicts additional details of the anatomical arrangement of the genital tract. The pertinent anatomy includes the body of the uterus 35 (from which the cervix 33 protrudes downward into the vagina 32), and including also the left and right ovaries 36 and 37 and left and right oviducts (Fallopian tubes) 38 and 39. The oviducts grow from the respective sides of the uterus 35, curving around the ovaries and ending, in the vicinity of the respective ovaries, in the funnel-like arrangements of the fimbria 310 and 311. The purpose of the fimbria 310 and 311 is to capture the egg when it ovulates by bursting out of one or the other ovary 36 or 37. This occurs at the time of ovulation and the egg then travels through the respective oviduct toward the uterus. Fertilization could occur if sperm have been injected into the vagina and if they traveled successfully through the cervix and uterus to meet and penetrate the egg in the oviduct, during the limited life-times of both the egg and the sperm.

FIG. 3A shows a probe 34 inserted so that neither of the electrodes, one of which is 5 seen as electrode 30, is in contact with the cervix; in this position, the electrodes are said to be in the lateral (or sideways) orientation. FIG. 3B shows the probe 34 in a different orientation, with electrode 30 touching the cervix 33. In FIG. 3B the electrodes are said to be in the anterior-dorsal (or forward-directed and backward-directed) orientation. The two different probe positions lead to two approximately parallel sets of diagnostic probe readings.

The probe 34 is inserted in the same manner as a vaginal tampon, and will naturally go as far as the posterior fornix region 31, at the upper end of the vaginal canal 32, in the upper and dorsal (backward-oriented) neighborhood of the protruding cervix 33. Without the guiding means such as provided by the protrusion 21 in FIG. 2, the electrode contact location was indeterminate. With the facility of guiding means such as provided by the protrusion 21 in FIG. 2, the insertion can be made in a controlled manner. The marked electrode (electrode 22 in FIG. 2, electrode 30 in FIG. 3B) can be placed in contact with a predetermined well-defined aspect of the epithelia in the posterior fornix region 31, as illustrated in FIGS. 3A and 3B.

Another method of achieving the controlled electrode orientation and epithelial contact is by altering the shape of the probe body so as to achieve the controlled contact by enhanced compliance with the detailed anatomy of the vaginal canal. Such a solution is merely an extension of the described method and is within the scope of this invention.

The shape of the electrodes need not be elongated as shown in FIGS. 2 and 3 but may take other forms such as circular disc, half-circle, square, etc. The size of the electrodes according to the invention is small relative to the vagina and comparable to the size of the cervical protrusion of the given mammal, here the human female. While the electrodes are not at all micro-electrodes (which would aim at individual cells), their size is such as to avoid a short-circuit contact with different macroscopic segments of the vaginal epithelium. The epithelium does have regions of different activities, caused for example by "pattern distributions" or differential localization of various oxidative enzymes with varied and phase of cycle dependent sensitivities to the steroid sex hormones. This is one of the characteristics that distinguish the probe of this invention from the probes of other inventors.

Other inventors' designs aimed to achieve the very opposite purpose of large contact area along at least a substantial part of the length of the vaginal canal and, with ring or spiral or helical electrodes, also with the circumferential dimension of the canal. Such designs short circuit across a number of distinct segments of the epithelium and therefore lose resolution, responding to an averaged charge-carrier, i.e., the electrolyte conductivity of the mucosal secretions.

The sufficiently small size of the electrodes is defined as allowing their placement so that the near end of the electrode further from the insertion end of the probe does not exceed about 100% to about 150% of the cervical protrusion into the fornix region. In this manner, the short circuiting across distinct segments of the epithelium is avoided.

Figure 4:
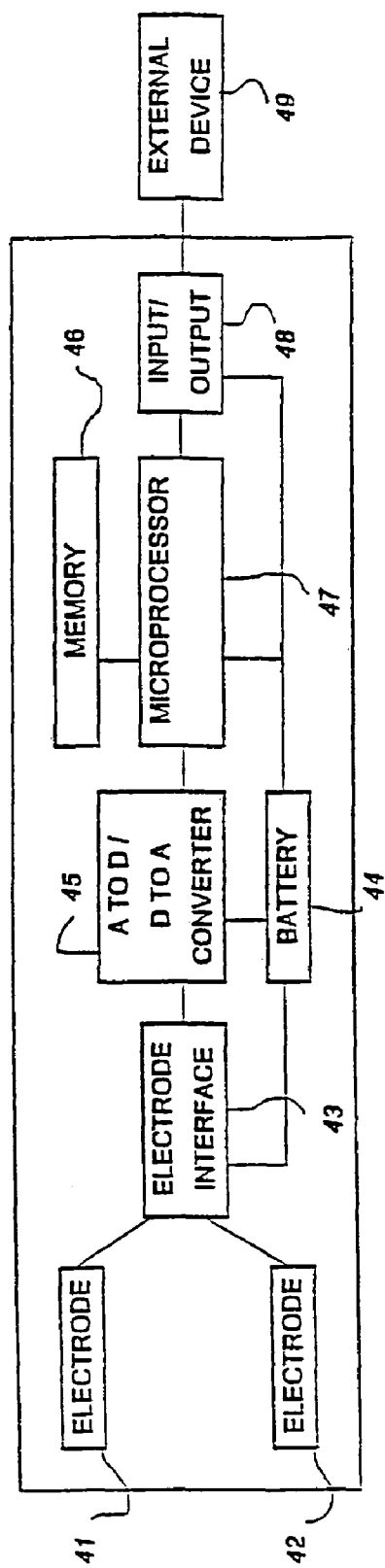
FIG. 4 is a block diagram of the electronic components of the vaginal probe of FIG. 2.

FIG. 4 is a block diagram of the electronic configuration of the probe of the invention. It represents a digital electronic implementation of the design discussed in my U.S. Pat. No. 4,753,247 with the added benefits of memory and external interface. Microprocessor 47 generates the waveform used in the probe measurement. The digitally generated waveform is converted into an analog signal in converter 45 and applied to the electrodes 41 and 42 via electrode interface conditioning electronics 43. The electrode response is similarly converted into digital data by the converter 45 for processing by microprocessor 47. The processed data is displayed on LCD or LED display (not shown) and stored in memory 46 for optional downloading at a later date via input/output interface 48 to external device 49, which can be a computer, for example.

Figure 5:
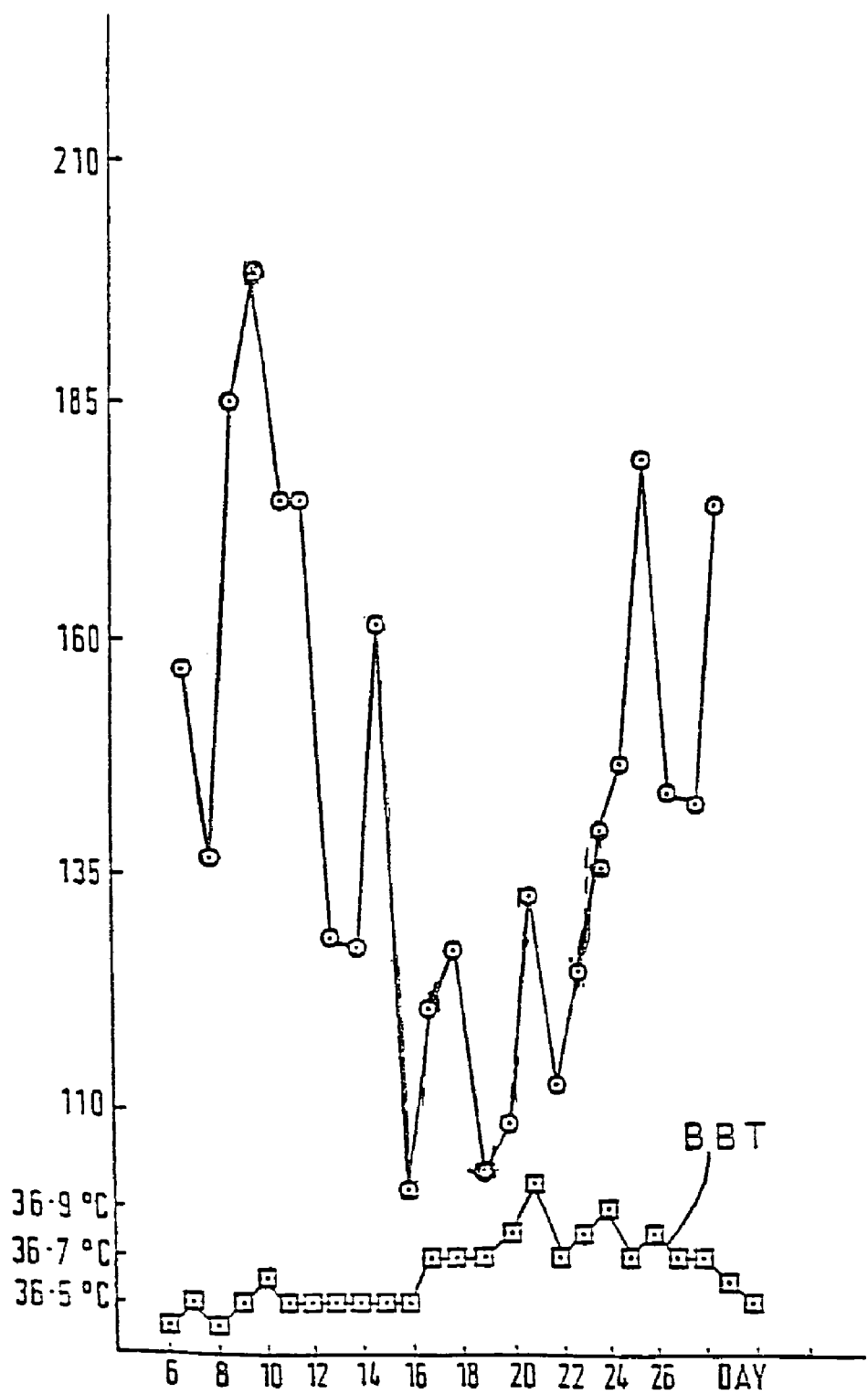
FIG. 5 is a graph of results obtained with the probe of my prior art, reproducing some of the results disclosed in my '247 patent.

Provided as a reference, FIG. 5 is a graph of one of the cyclic profiles obtained with the vitreous or glassy carbon electrode (gce) probe of my prior art by the first test subject of the project. I reproduce some of the data that were disclosed in my '247 patent, for the purpose of a comparison with the newly generated results reported here in support of the present application. In particular, FIG. 5 reproduces the one of the two consecutive cycles of FIG. 6 of the patent which was accompanied by the corresponding basal body temperature profile, with the temperature rise in evidence just after the probe ovulation-marker minimum on day 16 of the 29 days long menstrual cycle.

After the early follicular phase minimum on day 8, the probe profile of FIG. 5 shows clearly both the long-term and the short-term predictive peaks on days 10 and 15, respectively. The Figure also shows several post-ovulation peaks in the progesterone-controlled so-called luteal phase; characteristically, these post-ovulation peaks do not reach as high as the two predictive peaks in the estrogen-controlled follicular phase before ovulation.

A person skilled in the art of reproductive biology finds the oscillating or fluctuating pattern of peaks and dips in FIG. 5 generally consistent with the fact that the physiological characteristics of the genital tract fluctuate during the menstrual cycle. These peaks and dips—B absent in the conductometric curves of Weinmann and Zetek—occur as a result of complex inputs, including those from neural innervation, lymphatics and from the particularly well understood blood-borne ovarian steroid hormones whereby the ovulating ovary coordinates the various parts of the genital tract. The sex hormones act on the target organs through their action on specific receptor proteins, which function as signal transducers. The epithelia of the genital tract are known to undergo changes during the menstrual cycle, as observed, for example, by cytological methods.

With regard to the electronic admittance of the invention, electron microscopy has shown that the vaginal epithelial cells are interconnected by bridges of protoplasm and by tonofibrils, forming an integrated network. The microscopic anatomy of the vaginal mucosa is considered to be unique in its structure and in its responsiveness to the various hormones. The vaginal epithelium is a so-called uncornified stratified squamous type of multi-layered epithelium and it is known to undergo variations in its cells' characteristics during the menstrual cycle.

The invention replaces the visual observation of cytological methods with electrical measurements via the electrodes. An important aspect of the probe design is the capacitive coupling with the epithelial cells, achieved by means of controlled potential difference of very low amplitude and high frequency.

The low amplitude potential guarantees safety of operation because no electrolysis nor electrode metal dissolution can occur at the used 100 millivolt levels, well below the standard electrode potentials and/or overpotentials of reactions that can occur in the given physiological situation. This safety of operation is in contrast to the procedures involved in other inventors' prior art where voltage levels of several Volts are used and high currents are allowed to pass.

Also important for the design of the probe, which makes epithelial contact in the posterior fornix, is the fact that the fornix contains a squamocolumnar transitional zone of the epithelium. This is where the squamous epithelium gradually changes into the so-called simple columnar epithelium of the endocervix that produces the cervical mucus, also undergoing cyclical variations. Krantz (in "The Biology of the Cervix", edited by R. J. Blandau and K. Moghissi, The University of Chicago Press, 1973) invokes the meeting of the two types of epithelia as an area of change which varies from 1 to 10 mm in width in the same individual. There is a continuous process of epithelial breakdown and reparation, an evolution of cells into mature epithelium, which has been variously termed squamous metaplasia, epidermidization, reserve cell hyperplasia, and squamous prosoplasia. Herewith originates my expectation that the probe may detect early stages of cervical cancer and other pathologies.

Figure 6:
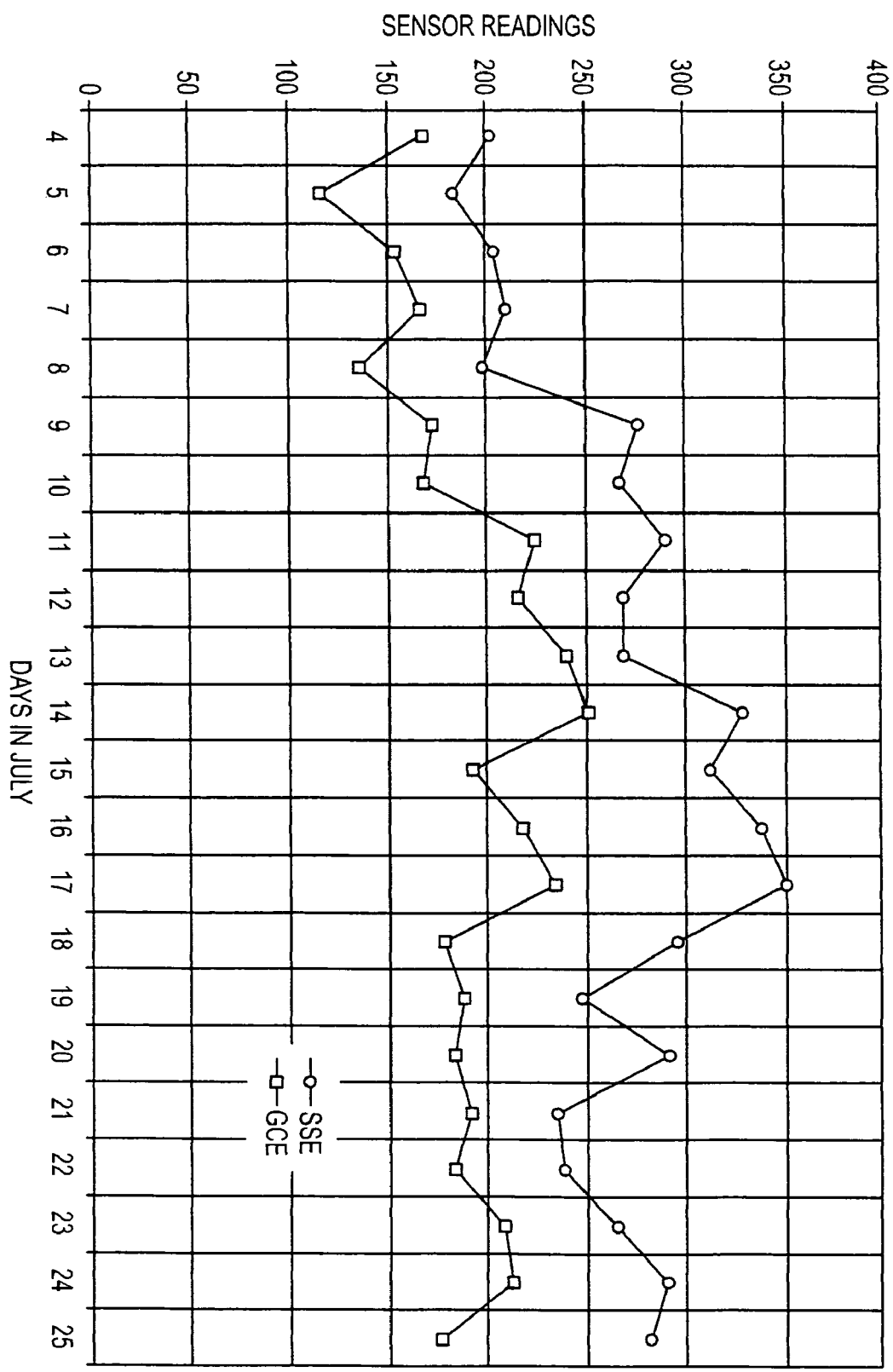
FIG. 6 is a graph of results obtained with the probe of the invention and with the probe of my prior art, in the first test subject of my prior art who is now of menopausal age and whose cycles are now artificially controlled by administered sex steroids that are involved in her Hormone Replacement Therapy (HRT).

FIG. 6 is evidence that the probe of the invention responds to the posterior fornix tissues in the same manner as the prior art probe, yielding a pseudo-menstrual cyclic profile of the same shape, the meaning of which is explained below. The Figure is also suggestive of an improved sensitivity in the new probe, and is the first of several comparative graphs of data that demonstrate the improvement.

FIG. 6 compares results obtained with the sse probe of the invention with results concurrently generated by the same subject with the old gce probe, using the same electronics in the comparison process and placing both probes in the same position, with the same electrode orientation. The same localized tissue contact was made with both probes.

The present electronics, and particularly its calibration, is not absolutely identical to the electronics that generated the data in FIG. 5 above. Consequently, quantitative comparisons of signal amplitudes are possible only within the presently generated results. Furthermore, the test subject of FIG. 6 is the same as in FIG. 5 but with a significant difference, which is reflected in the data: She is now of menopausal age and is receiving Hormone Replacement Therapy (HRT). Her pseudo-menstrual cycle is now controlled by the administered sex steroid hormones rather than by endogeneous, or naturally self-generated, hormones because after menopause the prQduction of the steroids by the ovaries has ceased.

The HRT cycle is referred to as a pseudo-menstrual cycle because, while the subject does exhibit menstruation-like bleeding at the end of the 25 days long cycle, this is induced by exogeneous (administered) steroids and she is no longer ovulating. The absence of ovulation is reflected in the profile of FIG. 6 as the absence of the mid-cycle ovulation-marker minimum. The standard HRT regimen of the exogeneous hormonal stimulation is as follows: Continuous administration of 1.25 mg of conjugated equine estrogens (Premarin brand) daily from day 1 of every month to day 25, opposed by added medroxyprogesterone (Provera brand) from day 15 to day 25. Hormone-withdrawal bleeding occurs at the end of the progesterone phase, in a manner reminiscent of the natural menstrual cycle.

FIG. 6 shows that both the gce probe of my prior art and the new sse probe of the present invention register the same shape of the profile for the tissue response, with the sse profile having higher amplitudes throughout. As can be expected, the continuous intake of the estrogens over the first 15 days causes an overall increase of the probe readings, in wave-like steps captured by both probes. The probes parallel each other remarkably well in capturing the pharmacokinetic profile. The new sse probe appears to be more sensitive to the effect of the progesterone "opposition treatment" in the second phase of the HRT cycle.

This and similar experimental results suggest that the probe of this invention should be useful as a human bioassay monitor for HRT management, and for the assessment of bioequivalence and efficacy of different HRT preparations. Such a tool is of great interest not only to physicians and their patients but also to the pharmaceutical industry. This is so for example because of the Food and Drug Administration's focus on the issues of bioequivalence, safety and efficacy of the sex hormone preparations; that focus has led to a recall of all generic conjugated equine estrogen products in 1991.

The probe of the invention should also be useful for the assessment of general health, and for the assessment of efficacy of various treatments in women's health care. A good example is the management of the premenstrual syndrome (PMS). PMS is a recurrent cyclic disorder, which includes luteal (that is post-ovulatory) phase-related changes in physiology, mood and/or behavior. The American Psychiatric Association calls the syndrome the premenstrual (formerly "the late luteal phase") dysphoric disorder and has defined its criteria in the Diagnostic and Statistical Manual of Mental Disorders (DSMMD). Statistically, although most women experience only mild cyclic symptoms, as many as 30-40% suffer troublesome symptoms that interfere with normal functioning, and in about 5% the symptoms are seriously disruptive.

For the psychiatrist, it is essential to establish that the various physiological and psychological dysfunctions vary with the menstrual cycle. It is important to separate patients who meet the DSMMD criteria from those who have exacerbations of somatic or psychiatric disorders during the postovulatory phase of the cycle, as well as from others who show fluctuations that are not related to the menstrual cycle. This is where the probe of the invention will become a psychiatrist's and psychotherapist's tool in the premenstrual assessment procedure.

Since progesterone therapy as well as oral contraceptives are common pharmacological interventions in PMS management, it is important to understand that these contraceptives exert their effect at multiple sites in the body. The sites include the hypothalamus and pituitary glands of the brain as well as the various parts of the genital tract depicted in FIG. 3A. However, it is generally impossible to pinpoint the one particular site of action of any given contraceptive preparation.

Figure 7:
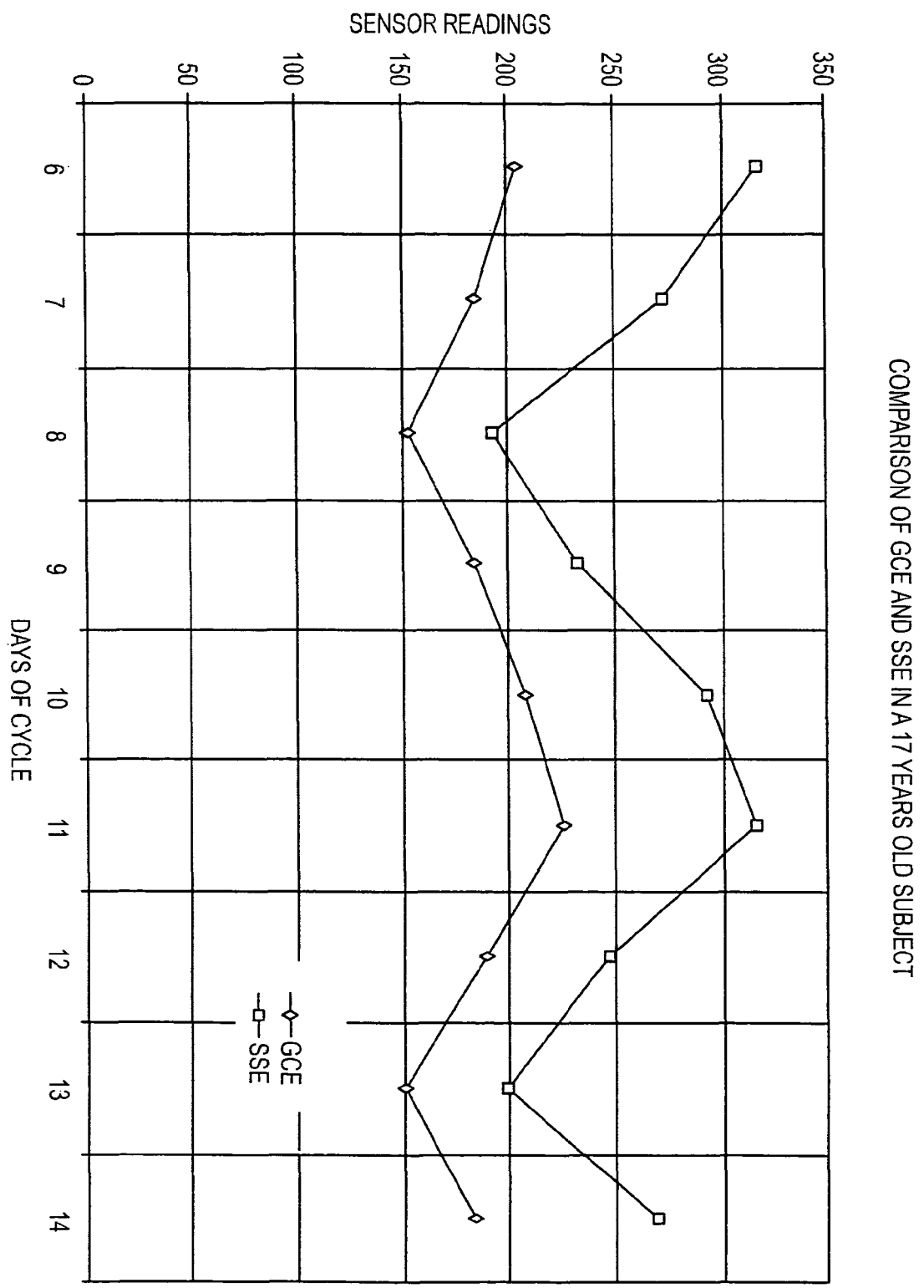
FIG. 7 is a graph of results obtained with the probe of the invention and with the probe of my prior art in a 17 years old adolescent female.

FIG. 7 depicts data from the pre-ovulation or follicular phase of a natural menstrual cycle, that is a menstrual cycle controlled by endogenous hormones naturally occurring in the female organism, rather than by hormones administered as medication. The graph in the Figure compares the sse probe of the invention with the gce probe of the prior art in a 17-year old adolescent female. This teenage subject has a history of highly irregular periods, which was attempted to be corrected by administration of triphasic-regimen contraceptive pills (Tri-Levlen 28 Tablets brand) in the three months before the reported medication-free experiment. (Tri-Levlen contains the estrogen ethinyl estradiol in three 7-day doses of 30, 40, and 50 micrograms, and the progesterone derivative levonorgestrel in doses of 50, 75, and 125 micrograms; the last 7 days are placebo, off therapy. These newer multiphasic contraceptive formulations are claimed to reproduce levels of estrogen in blood that resemble those found in the early follicular phase of the normal cycle). These facts mean that the subject will have—at least for now—cycles that may be natural but not typical or baseline. Nevertheless, the sse probe of the invention yields again, as in the HRT cycle in FIG. 6, the same shape of the profile as is concurrently generated by the gce probe of my prior art.

FIG. 7 shows that, as in the HRT cycle of FIG. 6, the amplitude of the sse probe data is consistently higher than the amplitude of the data from the prior art probe. Moreover, at least in this recorded part of the natural cycle of the teenage female, the probe of the invention displays a distinctly greater dynamic range B and consequently greater resolution which anticipates better reliability with respect to the probe of the prior art. In the record of the teenage cycle, albeit incomplete, both probes describe the same shape of the naturally controlled (i.e., endogenous hormones-driven) profile; this includes the expected features as exemplified by FIG. 5, namely the early follicular phase minimum on day 8 and the long-term predictive peak on day 11.

Even though the cyclic profile in FIG. 7 is incomplete, and even though the subject is not a mature adult, the results demonstrate the ovulation-predictive capability of the sse probe of the invention, and they also demonstrate the applicability of the invention to the monitoring of vaginal epithelia in females of widely different ages.

Comparing the results of the two subjects from the perspective of the widely different ages leads to the following observation. In the case of the menopausal female, the lateral (side-ways) orientation of the electrodes registers with both probes consistently higher readings than the anterior-dorsal (up-and-down) orientation. In the very young female, the opposite relationship between the orientations is observed, more pronounced with the more sensitive sse probe of the invention. This is consistent with an effect of aging on the epithelia, which can be expected (namely, atrophy in the menopausal epithelium), and the observation also adds to the importance of proper and consistent positioning means for the achievement of reproducible epithelial contact and measurements.

Figure 8:
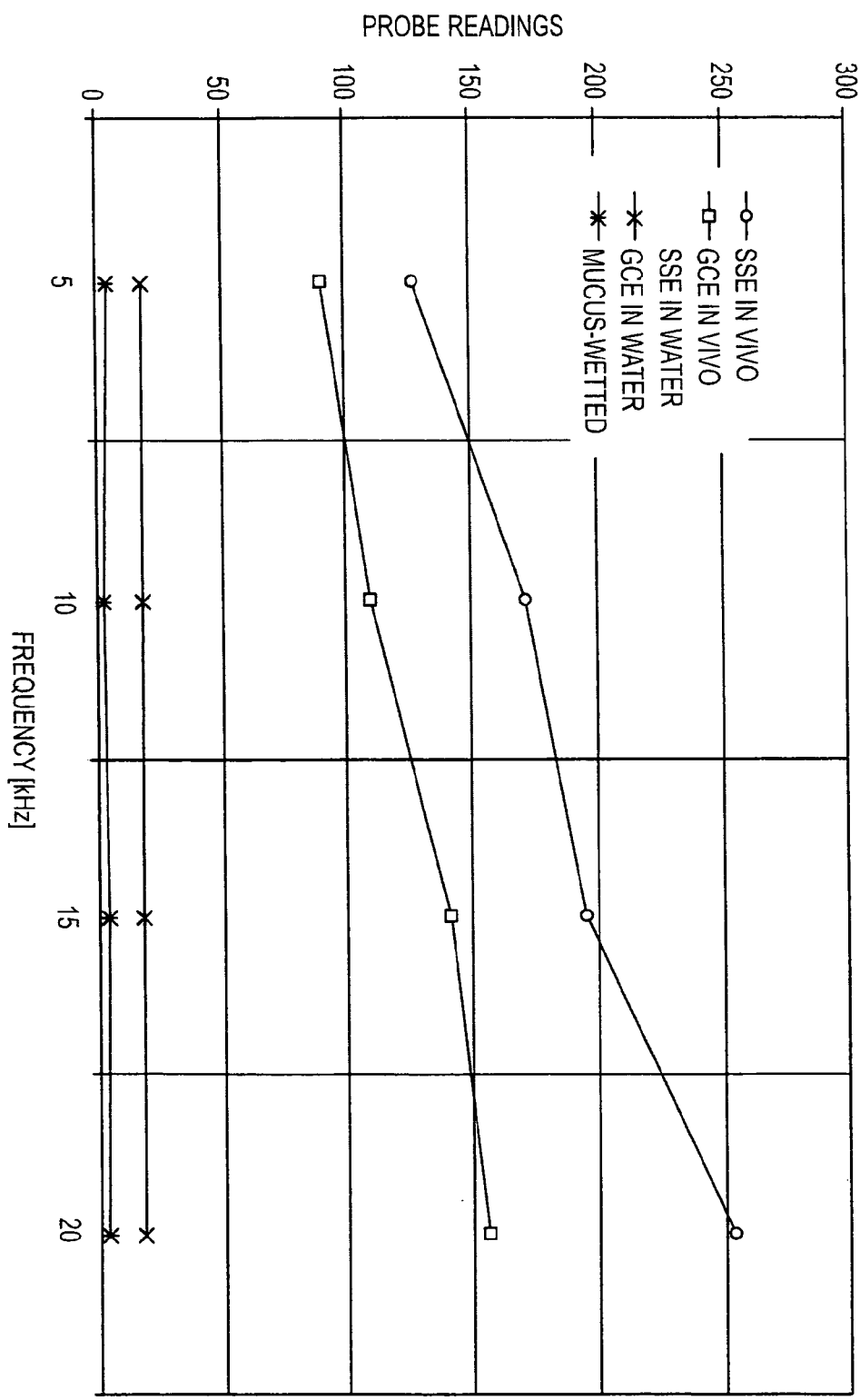
FIG. 8 is a comparative graph of respective frequency dependencies in vivo under exogeneous (HRT) estrogen stimulation, and of the practically identical frequency-independent responses in tap water, comparing the probe of the invention with the prior art probe.

FIG. 8 illustrates a frequency-dependence comparison of the probe of the invention with the prior art probe in terms of their responses with the estrogen-controlled (HRT) epithelium; both probes were in the anterior-ventral (up-and-down) electrode orientation in these experiments and the peak-to-peak voltage was 100 mV. The data indicate a higher sensitivity of the sse probe of the invention over the gce probe of the prior art.

FIG. 8 also demonstrates that in tap water both probes respond in a frequency-independent manner and, unlike in vivo, yield identical signal amplitudes. Scott et. al. obtained the same frequency independence in this frequency range in solutions of NaCl (0.01 M.1.0 M). The Figure further reports the fact that both probes give practically zero response, at all the frequencies, when they are wetted with the vaginal fluids and read after withdrawal from the vagina so that no contact is made with the epithelium of the posterior fornix.

The same observation of practically zero response after withdrawal was also made throughout the monitoring of the natural cycle data represented in FIG. 7 above. It was also observed that wiping the electrodes to dryness, before and/or after washing with soap and water, made no difference to the near-zero readings. The near-zero readings represent the zero of the instrumental set-up.

All this evidence means that the probes register a response of the epithelial tissues and that the conductivity of mucus in the vaginal lumen contributes very little, if anything, to the values of the probe readings. In other words, the vagina is not a simple tube, with insulating walls, filled with varying quantities of conductive fluids (such a model having been assumed in the conductometric prior art including Zetek's and Weinmann's).

It must be concluded that the mucus material adheres to the surface of the epithelium as its integral component rather than being transferred to the surface of the probe including the electrodes. This conclusion is consistent with Rosa and Velardo's findings of the mucins "capping the epithelium" during their investigations of histochemical localization of vaginal oxidative enzymes and mucins. Rosa and Velardo (Annals N.Y. Acad. Sci., Vol. 83, Art. 2, p. 122, Nov. 18, 1959) found differential localization or pattern distributions" of the oxidative enzymes in the vaginal epithelium. They also found these enzymes responsive to the steroid hormones in both synergistic and antagonistic manner, depending on the area and on the relative concentrations (which change with the phase of the cycle). They invoked "active and relatively inactive regions within the vaginal epithelium" in their studies of estrogen and progesterone effects on the oxidative metabolism and mucinogenesis of the component layers of the vaginal epithelium.

Figure 9:
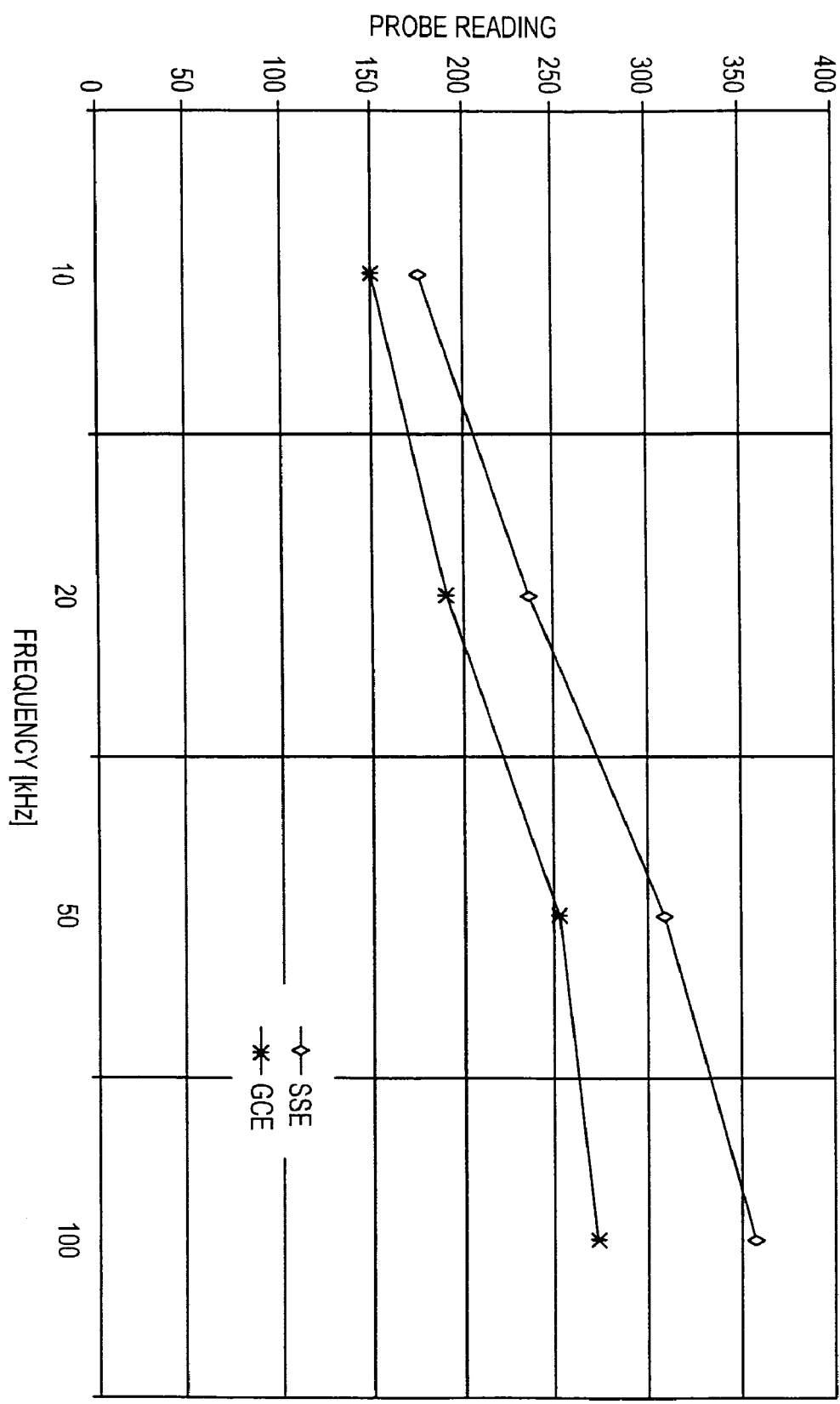
FIG. 9 is a comparative frequency-dependence graph of the two probes in vivo over a wider frequency range, obtained again with HRT estrogen-stimulated tissues, later in the estrogen phase.

FIG. 9 depicts the frequency-dependence comparison of the two probes over a range of frequencies extended upward, in measurements of the respective probes' response to estrogen-controlled epithelium, performed on another day of the HRT cycle with reference to the data in FIG. 8. This Figure confirms the conclusion of FIG. 8 as valid over an extended range of frequencies, which may be useful in the probe design implementation for various scientific and commercial applications.

FIGS. 10A and 10B illustrate a comparison between the sse probe of the invention (FIG. 10A) and the gce probe of the prior art (FIG. 10B) in terms of the respective XY plots of the data captured with an oscilloscope. The data were generated at 10 kHz, 100 mVpp in the anterior-ventral electrode orientation in vivo, with one probe after the other, on the same day of the estrogen-controlled phase of the HRT cycle (namely, day 14). The depicted data were therefore in fact generated on the day of the maximal estrogen effect on the epithelium, as reflected by the maximal readings by both probes in the data reported above in FIG. 6.

The XY plot data of FIGS. 10A and 10B were analyzed by comparing two features of the ellipsoid traces on the oscilloscope where X is the applied voltage and Y is the current response. One feature for comparison is the slope of the slanted axis of the ellipsoid that connects the extremes and goes through the origin; and the other feature for comparison is the distance (delta Y) between the points on the Y-axis where the ellipsoid intersects the Y-axis. The results of this comparison of the sse probe of the invention with the gce prior art probe are shown in the following Table.

| XY PLOT COMPARISON OF SSE AND GCE PROBES IN VIVO | | | |
|---|---|---|---|
| | SSE | GCE | SSE/GCE |
| SLOPE | 2.0 | 1.5 | 1.33 |
| DELTA Y | 72 | 54 | 1.33 |

This Table summarizes the results of one method of quantification of the superiority of the new sse probe over the old gce probe of my prior art.

FIG. 11 depicts the corresponding XY plot captured with an oscilloscope in tap water, using the sse probe of the invention. The gce probe of the prior art gave an identical result, both probes yielding the same slope of 0.2 and the same.

What is claimed is:

1. A method for tissue bioassay comprising the following steps:
   a) placing in a vagina of a female human an elongated probe having at least two metallic electrodes positioned close to an insertion end of said elongated probe, none of said at least two electrodes extends around the entire periphery of said elongate probe, wherein said probe is positioned so that at least one of said at least two metallic electrodes contacts an epithelium of a cervix or a fornix of said vagina of said female human;
   b) applying across said at least two metallic electrodes contacting said epithelium an alternating voltage;
   c) measuring across said at least two metallic electrodes an epithelium responsive parameter;
   d) generating a value of said epithelium responsive parameter representative of a hormonal status of said epithelium of said female human, and wherein use of said metallic electrodes to measure said epithelium responsive parameter increases amplitude of said value as compared to use of non-metallic electrodes;
   e) comparing said value of said epithelium responsive representative of said hormonal status of said epithelium of said female human to a reference value; and f) predicting an occurrence of ovulation in said female human.

2. The method of claim 1, wherein a peak-to-peak amplitude of said alternating voltage has a range of about 10 millivolts to about 900 millivolts.

3. The method of claim 1 wherein said value is selected from the group consisting of an admittance value, a current value, a voltage value, and a phase difference value.

4. The method of claim 1 wherein at least one of said electrodes is positioned at said insertion end of said probe.

5. The method of claim 1 wherein a distance between said insertion end of said probe and a proximal end of at least one of said metallic electrodes does not exceed about 100% to about 150% of a length of the cervical protrusion into the fornix region.

* * * * *